United States Patent
Weichselbaum et al.

(10) Patent No.: US 10,292,733 B2
(45) Date of Patent: May 21, 2019

(54) SPLIT BALLOON CATHETER FOR INTRA UTERINE INSEMINATION (IUI) AND SLOW RELEASE INSEMINATION (SRI)

(71) Applicants: LI-NOM MANAGEMENT LTD., Raanana (IL); Amnon Weichselbaum, Haifa (IL)

(72) Inventors: Amnon Weichselbaum, Haifa (IL); Yechiel Lisner, Raanana (IL)

( * ) Notice: Subject to any disclaimer, the term of this patent is extended or adjusted under 35 U.S.C. 154(b) by 63 days.

(21) Appl. No.: 15/536,250

(22) PCT Filed: Dec. 7, 2015

(86) PCT No.: PCT/IB2015/059416
§ 371 (c)(1),
(2) Date: Jun. 15, 2017

(87) PCT Pub. No.: WO2016/097924
PCT Pub. Date: Jun. 23, 2016

(65) Prior Publication Data
US 2017/0360478 A1 Dec. 21, 2017

Related U.S. Application Data

(60) Provisional application No. 62/093,556, filed on Dec. 18, 2014.

(51) Int. Cl.
| | | |
|---|---|---|
| A61B 17/43 | (2006.01) |
| A61D 19/02 | (2006.01) |
| A61M 25/00 | (2006.01) |
| A61M 25/10 | (2013.01) |
| A61B 17/00 | (2006.01) |
| A61B 90/00 | (2016.01) |

(52) U.S. Cl.
CPC ............ *A61B 17/43* (2013.01); *A61D 19/027* (2013.01); *A61M 25/00* (2013.01); *A61M 25/007* (2013.01); *A61M 25/0071* (2013.01); *A61M 25/0074* (2013.01); *A61M 25/10* (2013.01); *A61B 2017/00455* (2013.01); *A61B 2090/062* (2016.02); *A61B 2090/067* (2016.02); *A61B 2090/3937* (2016.02); *A61M 2025/0008* (2013.01); *A61M 2025/0079* (2013.01); *A61M 2205/0266* (2013.01)

(58) Field of Classification Search
CPC ....... A61B 17/43; A61M 25/00; A61D 19/027
USPC ...................................... 600/33–35
See application file for complete search history.

(56) References Cited

U.S. PATENT DOCUMENTS

| | | |
|---|---|---|
| 5,147,299 A | 9/1992 | Mendoza |
| 2003/0060800 A1 | 3/2003 | Ryan |
| 2005/0240211 A1 | 10/2005 | Sporri |
| 2009/0024108 A1 | 1/2009 | Lee-Sepsick |
| 2013/0144163 A1 | 6/2013 | Kumar |

FOREIGN PATENT DOCUMENTS

CN 2525951 12/2002

OTHER PUBLICATIONS

PCT Written Opinion PCT/IB2015/059416, dated Mar. 31, 2016.

*Primary Examiner* — John P Lacyk
(74) *Attorney, Agent, or Firm* — Dekel Patent Ltd.; David Klein

(57) ABSTRACT

An assembly includes a catheter that has an insemination lumen for injecting sperm into a uterus. The insemination lumen includes two branches (sub-lumens), one directed toward a left ostium and the other directed to a right ostium of fallopian tubes.

9 Claims, 6 Drawing Sheets

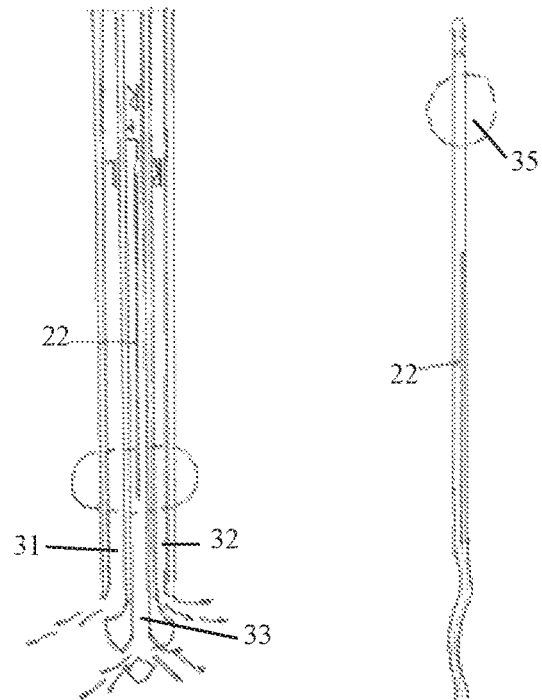
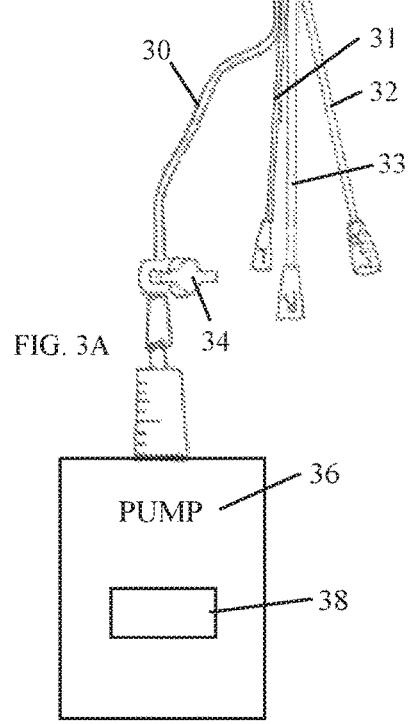
FIG. 3B
FIG. 3A

US 10,292,733 B2

SPLIT BALLOON CATHETER FOR INTRA UTERINE INSEMINATION (IUI) AND SLOW RELEASE INSEMINATION (SRI)

FIELD OF THE INVENTION

The present invention relates to catheters for Intra Uterine Insemination (IUI) and Slow Release Insemination (SRI).

BACKGROUND OF THE INVENTION

Artificial insemination may be accomplished by several techniques, such as intrauterine insemination or slow release insemination. Intrauterine insemination may be preferable to cervical insemination, because the cervical canal may be hostile due to various factors, such as viscous mucus, acidic mucus, infections, and sperm antibodies. Another reason may be a significant loss of semen that flows down to the vagina. However, intrauterine insemination has disadvantages as well, such as loss of sperm material to the cervix and vagina.

Although many solutions have been proposed to improve IUI, these solutions are far from perfect.

SUMMARY OF THE INVENTION

The present invention seeks to provide improved catheters for IUI and SRI, as is described more in detail further below.

The invention also seeks to provide a microfluidic pumping device for slow release insemination or administration of medicine and biological and pharmaceutical materials. The pump is compatible with a split balloon catheter for Intra Uterine Insemination (IUI), and can divide the sperm reservoir into aliquots. Consequently, the pump can deliver sperm to the left or right fallopian tubes or simultaneously to both fallopian tubes in predetermined volume relations.

IUI has the advantages of bypassing the hostile environment of the cervix and shortening the distance between the sperm and the ovum. The use of a balloon catheter for insemination has the advantage of preventing loss of sperm material to the cervix and vagina. SRI has the advantage of increasing the time window of opportunity for fertilization. The balloon insemination catheter of the present invention combines all the above advantages because it bypasses the cervix, directs sperm to the left and/or right fallopian tubes in predetermined volume relations, and prevents leakage of sperm. The invention is compatible with slow release insemination devices.

BRIEF DESCRIPTION OF THE DRAWINGS

The present invention will be understood and appreciated more fully from the following detailed description, taken in conjunction with the drawings in which:

FIGS. 3A-3B are simplified pictorial illustrations of a catheter for IUI, in accordance with another non-limiting embodiment of the present invention.

DETAILED DESCRIPTION OF EXEMPLARY EMBODIMENTS

Figure 1A:
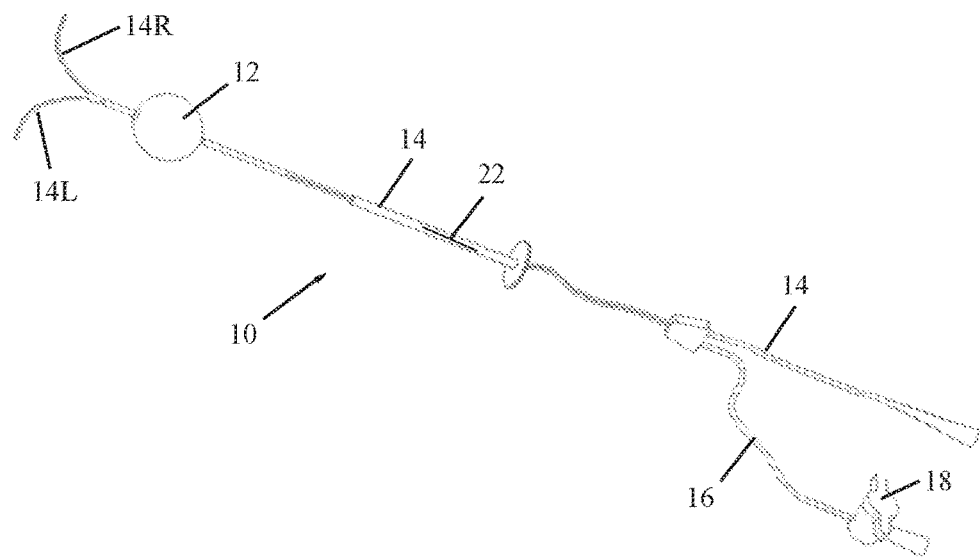
FIGS. 1A-1E are simplified pictorial illustrations of a catheter assembly for IUI, constructed and operative in accordance with a non-limiting embodiment of the present invention.

Reference is now made to FIGS. 1A-1E, which illustrate a catheter assembly for IUI and SRI, constructed and operative in accordance with a non-limiting embodiment of the present invention.

The assembly includes a catheter 10 and a balloon 12 mounted on the catheter 10. The catheter has two separated channels or lumens 14 and 16 running down its length. Catheter 10 is used to access the uterine cavity for sperm injection into the uterus (through one lumen), towards the fallopian tubes.

The first lumen 14 (insemination lumen 14) is used to inject washed sperm into the uterus during IUI or SRI procedures. The second lumen 16 (inflation lumen 16) has a valve 18 on the outside end and connects to balloon 12 near the distal tip. Balloon 12 is inflated by a syringe (not shown) with sterile water or air when it lies inside the uterus, in order to stop it from slipping out and for prevention of sperm leakage to the cervix.

The part of the insemination lumen 14 that protrudes beyond the inflatable balloon 12 splits into two branches (two sub lumens) 14L and 14R. One is directed toward the left ostium (orifice) and the other to the right ostium of the fallopian tubes.

Figure 1B:
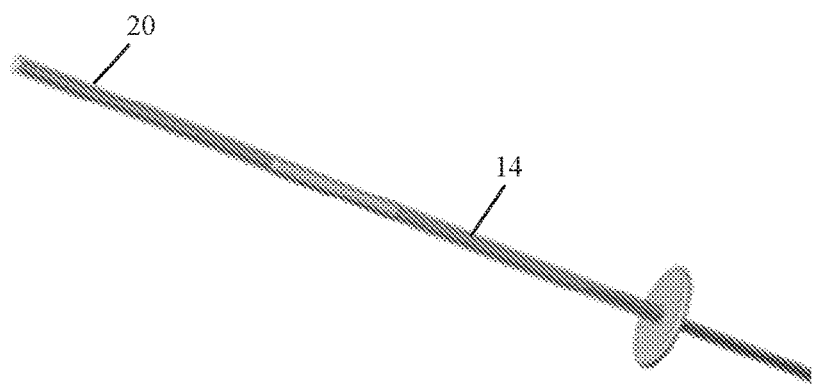
Figure 1C:
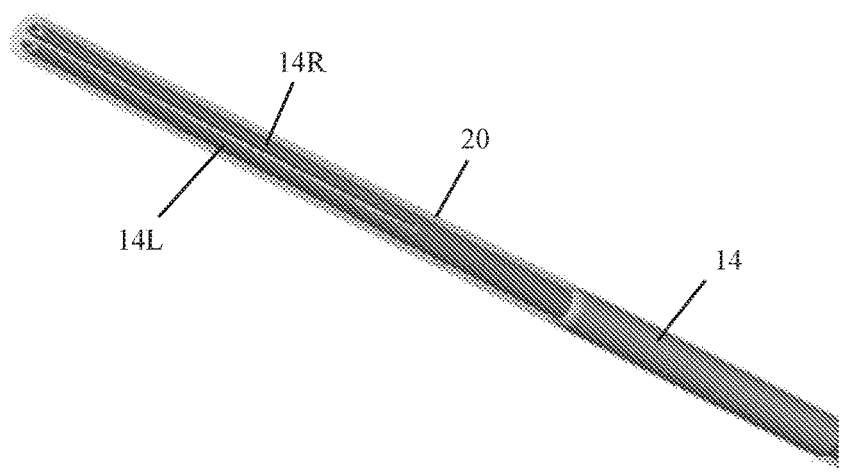
Figure 1D:
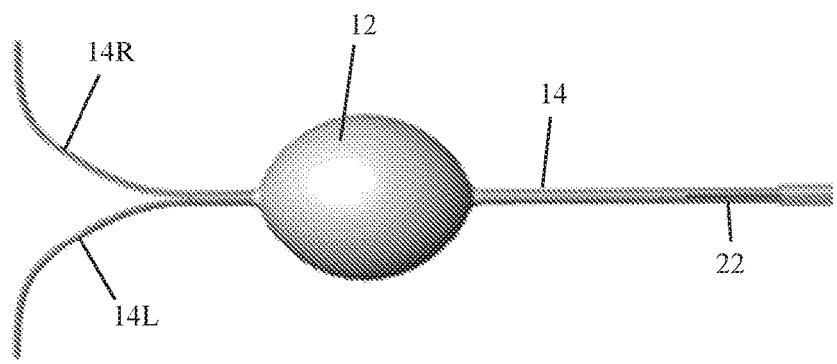
Figure 1E:
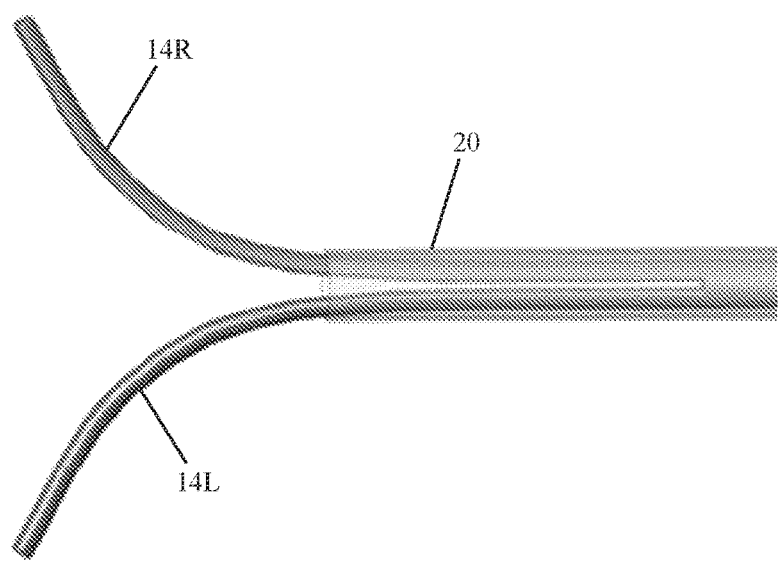

During insertion of the catheter 10 through the cervix into the uterine cavity, the two branches 14L and 14R are attached by an elongated sleeve 20 (FIG. 1B and enlarged in FIG. 2C). After insertion, the sleeve 20 is pulled back, and as a result the two branches 14L and 14R are separated and move toward the left and right orifices of the fallopian tubes (as seen in FIG. 2D and in the enlarged view of FIG. 2E).

Alternatively, the branches 14L and 14R can be made of a shape-memory material (alloy) that "remembers" its original, cold-forged shape (such as NITINOL wire). In such an embodiment, the two branches are close to each other during insertion of the catheter into the uterine cavity, and immediately after insertion, in which the environment is warmer, separate from each other and move towards the left and right orifices of the fallopian tubes.

A fiducial mark 22 (FIGS. 1A and 1D) along the shaft of the catheter 10 enables the clinician to align the catheter properly (both in terms of angular orientation and depth) and as a result to inject the sperm simultaneously toward the left and right ostium of the fallopian tube.

In an alternate embodiment of the invention, there is no balloon and the sperm is delivered through the branches as described above.

Figure 2A:
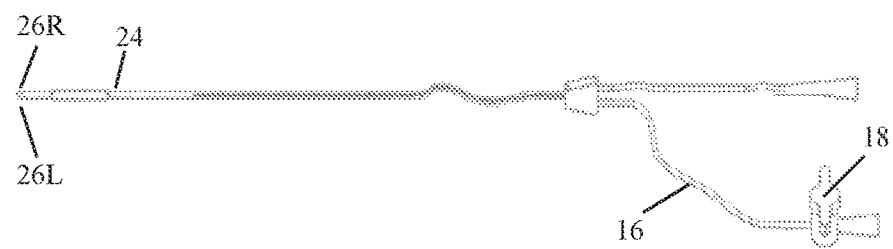
FIGS. 2A-2B are simplified pictorial illustrations of a double sided hole catheter for IUI, constructed and operative in accordance with a non-limiting embodiment of the present invention.
Figure 2B:
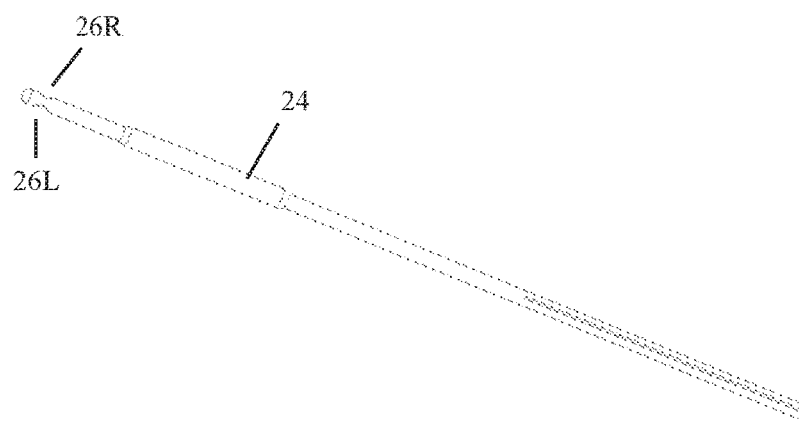

Reference is now made to FIGS. 2A-2B, which illustrate another catheter assembly for IUI and SRI, constructed and operative in accordance with a non-limiting embodiment of the present invention. In this embodiment, the split portion is replaced by a double-sided hole catheter 24, i.e. two holes 26L and 26R near the tip of the catheter (directed towards the left and to the right when the fiducial mark is facing up).

Reference is now made to FIGS. 3A-3B, which illustrate another catheter assembly for IUI and SRI, constructed and operative in accordance with a non-limiting embodiment of the present invention. In this embodiment, the catheter has four separated channels or lumens 30, 31, 32 and 33 extending down its length. The first lumen 30 has a valve 34 on the outside end and connects to a balloon 35 near the tip. The balloon 35 may be inflated by a syringe (not shown) with sterile water or air when it lies inside the uterus, in order to stop it from slipping out and for prevention of sperm leakage to the cervix.

The second lumen 31 is used to inject washed sperm into the uterus toward the left (L) fallopian tube during IUI or SRI procedures (the second lumen 31 is the first insemination lumen—its luer lock connector marked with the letter L).

The third lumen 32 is used to inject washed sperm into the uterus toward the right (R) fallopian tube during IUI or SRI procedures (the third lumen 32 is the second insemination lumen—its luer lock connector marked with the letter R).

The fourth lumen 33 is used to inject washed sperm into the uterus simultaneously toward the right (R) and left (L) fallopian tubes during IUI or SRI procedures (the fourth lumen 33 is the third insemination lumen—its luer lock connector marked with the letters L+R).

As seen in FIG. 3A, a microfluidic pumping device 36 may be in fluid communication with one of the lumens, such as first lumen 30, for slow release insemination or administration of medicine and biological and pharmaceutical materials. Pump 36 can divide the sperm reservoir into aliquots. Accordingly, pump 36 can deliver sperm to the left or right fallopian tubes or simultaneously to both fallopian tubes in predetermined volume relations.

For example, if the ultrasonic examination reveals follicles only in the right ovary, then the sperm will be directed only towards the right fallopian tube; if both ovaries display follicles in a proportion of 4:1 (8 follicles in the right ovary and 2 in the left), then the sperm will be delivered accordingly, i.e., 80% to the right fallopian tube and 20% to the left one.

Pump 36 can be provided with a processor 38 for calculating the distribution of sperm to the left or right fallopian tubes or both tubes. Processor 38 may be manually fed the data or may be in direct communication with the database of the imaging (e.g., ultrasonic imaging) device that images the ovaries.

Figures 4A, 4B:
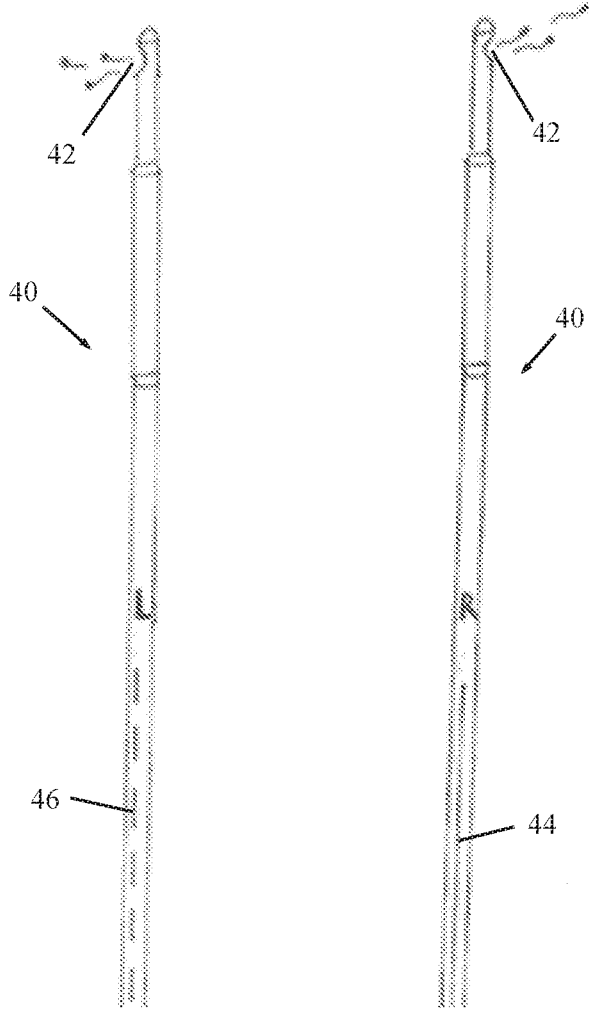
FIGS. 4A-4B are simplified pictorial illustrations of a catheter for IUI, in accordance with yet another non-limiting embodiment of the present invention.

Reference is now made to FIGS. 4A-4B, which illustrate another catheter assembly for IUI and SRI, constructed and operative in accordance with a non-limiting embodiment of the present invention. In this embodiment, the catheter 40 has one side aperture 42 with two different fiducial markers or lines 44 and 46. The two different fiducial markers or lines 44 and 46 make it easy to differentiate use for the left or right fallopian tube. For example, without limitation, fiducial line 44 may be a continuous line with the letter R (for directing sperm towards the right fallopian tube) and the fiducial line 46 may be a dashed or other broken line with the letter L (to direct sperm towards the left fallopian tube). The two different fiducial markers or lines 44 and 46 may be angularly spaced from one another by 180°.

This catheter with the single-side aperture can be a balloon catheter or a catheter without an anchor balloon.

What is claimed is:

1. An assembly comprising:
   a catheter comprising an insemination lumen for injecting sperm into a uterus, wherein said insemination lumen comprises two branches, one of said branches directed toward a left ostium and the other of said branches directed to a right ostium of fallopian tubes; and
   a fiducial mark on said catheter that indicates angular orientation and depth orientation of said catheter and said branches, wherein a balloon is mounted on a distal portion of said catheter, and said catheter further comprises an inflation lumen connected to said balloon for inflating said balloon, and wherein part of said insemination lumen protrudes distally beyond said balloon and then splits into said two branches.

2. The assembly according to claim 1, wherein said fiducial mark comprises two different fiducial marks or lines angularly spaced from one another by 180°.

3. The assembly according to claim 1, further comprising a movable sleeve disposed over said branches, wherein upon suitable movement of said sleeve, said branches separate from each other.

4. The assembly according to claim 1, wherein said branches are made of a shape memory material.

5. The assembly according to claim 1, wherein said fiducial mark comprises two different fiducial marks angularly spaced from one another.

6. The assembly according to claim 1, wherein said branches of said insemination lumen are left and right holes near a tip of said catheter.

7. The assembly according to claim 1, wherein said insemination lumen comprises three insemination lumens, a first insemination lumen for directing sperm to the left fallopian tube, a second insemination lumen for directing sperm to the right fallopian tube, and a third insemination lumen for directing sperm to the left and right fallopian tubes.

8. The assembly according to claim 7, further comprising a microfluidic pumping device in fluid communication with one of the lumens.

9. The assembly according to claim 7, further comprising a processor operative to calculate a distribution of sperm to the left or right fallopian tubes or both tubes.

\* \* \* \* \*